US011561140B2

(12) United States Patent
Kobayashi et al.

(10) Patent No.: US 11,561,140 B2
(45) Date of Patent: Jan. 24, 2023

(54) DETERIORATION EVALUATION METHOD

(71) Applicant: SINTOKOGIO, LTD., Nagoya (JP)

(72) Inventors: Yuji Kobayashi, Toyokawa (JP); Akinori Matsui, Toyokawa (JP)

(73) Assignee: SINTOKOGIO, LTD., Nagoya (JP)

(*) Notice: Subject to any disclaimer, the term of this patent is extended or adjusted under 35 U.S.C. 154(b) by 0 days.

(21) Appl. No.: 17/291,148

(22) PCT Filed: Jul. 26, 2019

(86) PCT No.: PCT/JP2019/029539
§ 371 (c)(1),
(2) Date: May 4, 2021

(87) PCT Pub. No.: WO2020/095485
PCT Pub. Date: May 14, 2020

(65) Prior Publication Data
US 2022/0065718 A1    Mar. 3, 2022

(30) Foreign Application Priority Data

Nov. 7, 2018   (JP) .............................. JP2018-209560

(51) Int. Cl.
*B24C 1/10*   (2006.01)
*G01L 1/25*   (2006.01)
*G01N 33/2045*   (2019.01)

(52) U.S. Cl.
CPC ................. *G01L 1/25* (2013.01); *B24C 1/10* (2013.01); *G01N 33/2045* (2019.01)

(58) Field of Classification Search
CPC ......... G01L 1/25; B24C 1/10; G01N 33/2045; G01N 33/20
See application file for complete search history.

(56) References Cited

U.S. PATENT DOCUMENTS 9,056,386 B2 *   6/2015  Kobayashi .............. C21D 7/06
9,486,894 B2 *  11/2016  Kobayashi .............. B24C 1/10
(Continued)

FOREIGN PATENT DOCUMENTS

| JP | H07-092140 A | 4/1995 |
| JP | H08-043326 A | 2/1996 |

(Continued)

OTHER PUBLICATIONS

International Preliminary Report on Patentability dated May 20, 2021 for PCT/JP2019/029539.

(Continued)

*Primary Examiner* — Ryan J. Walters
(74) *Attorney, Agent, or Firm* — Faegre Drinker Biddle & Reath LLP

(57) ABSTRACT

A deterioration evaluation method includes a determination step of determining a shot peening condition for imparting a maximum residual stress to an object formed of a metal material; a first shot peening step of performing first shot peening on the object under the shot peening condition; a first measurement step of measuring a first residual stress of the object after the first shot peening step; a second shot peening step of performing second shot peening on the object after the first measurement step under the shot peening condition; a second measurement step of measuring a second residual stress of the object after the second shot peening step; and an evaluation step of evaluating deterioration of the object based on the first residual stress and the second residual stress.

11 Claims, 6 Drawing Sheets

(56) References Cited

U.S. PATENT DOCUMENTS

| | | | |
|---|---|---|---|
| 10,048,227 B2 * | 8/2018 | Makino | G01N 27/9046 |
| 2010/0239068 A1 | 9/2010 | Belassel et al. | |
| 2010/0300168 A1 * | 12/2010 | Ishikura | C21D 7/06 |
| | | | 72/53 |
| 2013/0118220 A1 * | 5/2013 | Kobayashi | C21D 7/06 |
| | | | 72/53 |

FOREIGN PATENT DOCUMENTS

| | | |
|---|---|---|
| JP | 2004-045115 A | 2/2004 |
| JP | 2004-069659 A | 3/2004 |
| JP | 2011-033582 A | 2/2011 |
| JP | 2013-108952 A | 6/2013 |
| JP | 2017-9356 A | 1/2017 |
| JP | 2018-141703 A | 9/2018 |

OTHER PUBLICATIONS

Okada, Hideki, "Relationship among specimen's hardness, residual stress distribution and yield stress on the difference of shot peening methods," Journal of High Pressure Institute of Japan, vol. 41, No. 5, 2003, p. 233-p. 242.

Kobayashi, Yuji, "Influences of Mechanical Properties and Retained Austenite Content on Shot-peening Characteristics," Transactions of Japan Society of Spring Engineers, No. 57, 2012, p. 9-p. 15.

* cited by examiner

DETERIORATION EVALUATION METHOD

TECHNICAL FIELD

The present disclosure relates to a deterioration evaluation method.

BACKGROUND ART

Shot peening of projecting projection materials (shot media) having a high hardness onto a surface of an object formed of a metal material is known (for example, Non-Patent Literature 1 and 2). According to shot peening, the fatigue strength of the metal material can be improved.

Shot peening is effective in improving the life of products formed of metal materials. For example, the destruction of a mold often occurs due to a heat check (a heat crack) caused by repeatedly undergoing thermal expansion and contraction. According to shot peening, it is possible to suppress the heat check of the mold. If the life of the mold is improved by shot peening, it is possible to reduce the mold cost included in the manufacturing cost of the product.

A method of evaluating the fatigue of a metal material by applying a load to a test piece is described in Patent Literature 1 and 2. By evaluating the fatigue of the metal material, it is possible to check the timing of mold maintenance or replacement, for example.

CITATION LIST

Patent Literature

[Patent Literature 1] Japanese Unexamined Patent Publication No. 2004-69659
[Patent Literature 2] Japanese Unexamined Patent Publication No. 2013-108952

Non-Patent Literature

[Non-Patent Literature 1] Yuji Kobayashi, "Influences of mechanical properties and retained austenite content on shot peening characteristics," Spring papers, No. 57, P. 9-15, 2012
[Non-Patent Literature 2] Hideki Okada, "Relationship among specimen's hardness, residual stress distribution and yield stress on the difference of shot peening methods," Pressure technology, volume 41, No. 5, P. 223-242, 2003

SUMMARY OF INVENTION

Technical Problem

The methods described in Patent Literature 1 and 2 involve a destructive test. Therefore, there is a demand for a method of evaluating the deterioration of a metal material in a non-destructive manner.

The present disclosure provides a deterioration evaluation method capable of evaluating the deterioration of a metal material in a non-destructive manner.

Solution to Problem

According to research conducted by the present inventors, it is understood that when an object formed of a metal material deteriorates, even if shot peening is performed under a shot peening condition for imparting the maximum residual stress and the maximum half-value range, the values of the residual stress and the half-value range which are measured after the shot peening decrease.

A deterioration evaluation method according to the present disclosure includes a determination step of determining a shot peening condition for imparting a maximum residual stress to an object formed of a metal material; a first shot peening step of performing first shot peening on the object under the shot peening condition; a first measurement step of measuring a first residual stress of the object after the first shot peening step; a second shot peening step of performing second shot peening on the object after the first measurement step under the shot peening condition; a second measurement step of measuring a second residual stress of the object after the second shot peening step; and an evaluation step of evaluating deterioration of the object based on the first residual stress and the second residual stress.

In the deterioration evaluation method, the phenomenon that when the object formed of the metal material deteriorates, even if the shot peening is performed under the shot peening condition for imparting the maximum residual stress, the value of the residual stress which is measured after the shot peening decreases is used. Therefore, it is possible to evaluate the deterioration of the metal material forming the object in a non-destructive manner based on the first residual stress measured after the first shot peening and the second residual stress measured after the second shot peening.

A deterioration evaluation method according to the present disclosure includes a determination step of determining a shot peening condition for imparting a maximum half-value range to an object formed of a metal material; a first shot peening step of performing first shot peening on the object under the shot peening condition; a first measurement step of measuring a first half-value range of the object after the first shot peening step; a second shot peening step of performing second shot peening on the object after the first measurement step under the shot peening condition; a second measurement step of measuring a second half-value range of the object after the second shot peening step; and an evaluation step of evaluating deterioration of the object based on the first half-value range and the second half-value range.

In the deterioration evaluation method, the phenomenon that when the object formed of the metal material deteriorates, even if the shot peening is performed under the shot peening condition for imparting the maximum half-value range, the value of the half-value range which is measured after the shot peening decreases is used. Therefore, it is possible to evaluate the deterioration of the metal material forming the object in a non-destructive manner based on the first half-value range measured after the first shot peening and the second half-value range measured after the second shot peening.

In the deterioration evaluation method according to one embodiment, in the determination step, the shot peening condition may be determined based on a hardness of the object. In this case, the shot peening condition can be appropriately determined.

In the deterioration evaluation method according to one embodiment, in the first measurement step and the second measurement step, a measurement may be performed by a diffraction method. In this case, the measurement can be appropriately performed.

In the deterioration evaluation method according to one embodiment, the object may be formed of a steel material.

In this case, since steel materials are widely used, there is a high need for the deterioration evaluation method.

Advantageous Effects of Invention

According to the deterioration evaluation method according to the present disclosure, it is possible to evaluate the deterioration of a metal material in a non-destructive manner.

DESCRIPTION OF EMBODIMENTS

Figure 1:
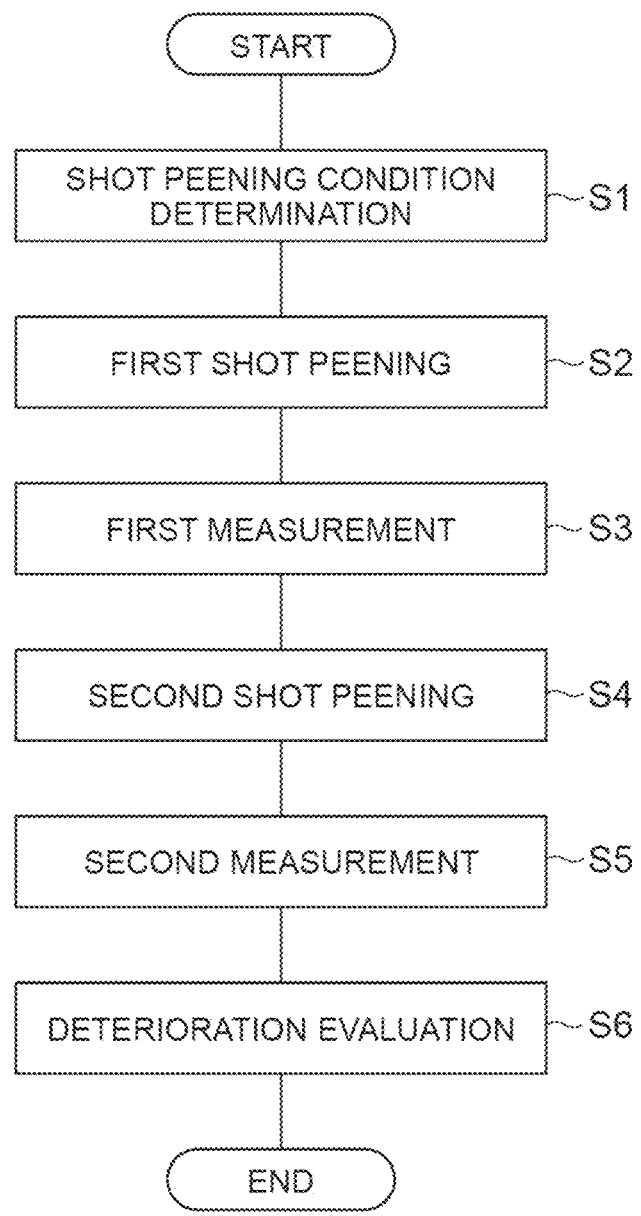
FIG. 1 is a flowchart showing a deterioration evaluation method according to an embodiment.

Hereinafter, embodiments will be described in detail with reference to the accompanying drawings. In the description, the same reference numerals are used for the same elements or elements having the same function, and duplicate description is omitted.

FIG. 1 is a flowchart showing a deterioration evaluation method according to an embodiment. The deterioration evaluation method according to the embodiment is a method of evaluating the deterioration of an object formed of a metal material in a non-destructive manner. The metal material forming the object is, for example, a steel material. Specific examples of the steel material include a medium carbon quenching material having a carbon content of 0.5% to 0.6%, a high carbon carburized material having a carbon content of 0.8% to 1.1%, and the like. The medium carbon hardened material is used as, for example, a spring material and a mold material for aluminum die casting. The high carbon carburized material is used as, for example, a gear material. All of these steel materials are martensitic steels having a martensitic structure.

This deterioration evaluation method includes step S1 (a determination step) of determining a shot peening condition, step S2 (a first shot peening step) of performing first shot peening, step S3 (a first measurement step) of measuring a first residual stress, step S4 (a second shot peening step) of performing second shot peening, step S5 (a second measurement step) of measuring a second residual stress, and step S6 (an evaluation step) of evaluating the deterioration of the object.

For example, step S1, step S2, and step S3 are performed at the time of manufacturing the object, and steps S4, step S5, and step S6 are performed at the time of maintenance of the object. Accordingly, during maintenance of the object, it is possible to evaluate the deterioration of the metal material forming the object in a non-destructive manner. Hereinafter, each step will be described.

In step S1, the shot peening condition for imparting the maximum residual stress to the object is determined. The maximum residual stress is the maximum value of the residual stress (a compressive residual stress) that can be imparted to the object. The maximum residual stress depends on the object.

In the shot peening, the residual stress to be imparted to the object can be increased by increasing the hardness of shot medium. However, if the hardness of the object does not match the hardness of the shot medium, the residual stress to be imparted to the object may actually be reduced by increasing the hardness of the shot medium. That is, to impart the maximum residual stress to the object, it is necessary to optimize the balance between the hardness of the object and the hardness of the shot medium.

To impart the maximum residual stress to the object, for example, the hardness of the shot medium is set higher than the hardness of the object within a range of 50 HV (Vickers hardness) or more and 250 HV or less. By setting the difference to 50 HV or more, it is possible to impart the residual stress to a surface portion of the object. If the difference is set higher than 250 HV, the energy of projection is used for scraping a surface of the object, and the residual stress cannot be effectively and stably imparted to the surface portion of the object. As the scraping amount increases, the change amount in dimension of the object increases. By setting the scraping amount of the object to 5 μm or less, it is possible to effectively and stably impart the residual stress to the surface portion of the object, and to suppress the change in the dimensions of the object.

However, if the hardness of the object is lower than 750 HV, it may not be possible to impart a sufficient residual stress to the surface portion of the object. The hardness of an object is, for example, the hardness of the surface portion from the surface of the object to a depth of 0.050 mm. The shot peening condition determined in step S1 may be a condition other than the hardness of the shot medium as long as it is a condition for imparting the maximum residual stress.

The particle size of the shot medium can be 0.05 mm or more and 0.6 mm or less. By setting the particle size of the shot medium to 0.05 mm or more, it is possible to easily produce the shot medium. By setting the particle size of the shot medium to 0.6 mm or less, it is possible to make a position where the residual stress shows the maximum value in a depth direction (a peak position) not too deep, and to make the peak position within 100 μm from the surface of the object. By making the peak position fall within this range, the fatigue strength of the object can be effectively improved.

In step S2, the first shot peening is performed on the object under the shot peening condition determined in step S1. Accordingly, the residual stress is imparted to the surface portion of the object.

In step S3, the first residual stress of the object after the first shot peening (that is, after step S2) is measured. In step S3, the measurement is performed by a diffraction method, for example. Specific examples of the diffraction method include an X-ray diffraction method, an electron beam diffraction method, a neutron diffraction method, and the like. The measurement method by the X-ray diffraction method is disclosed in, for example, Japanese Unexamined Patent Publication No. 2017-009356. In step S3, the measurement may be performed by a positron annihilation method.

Figure 2:
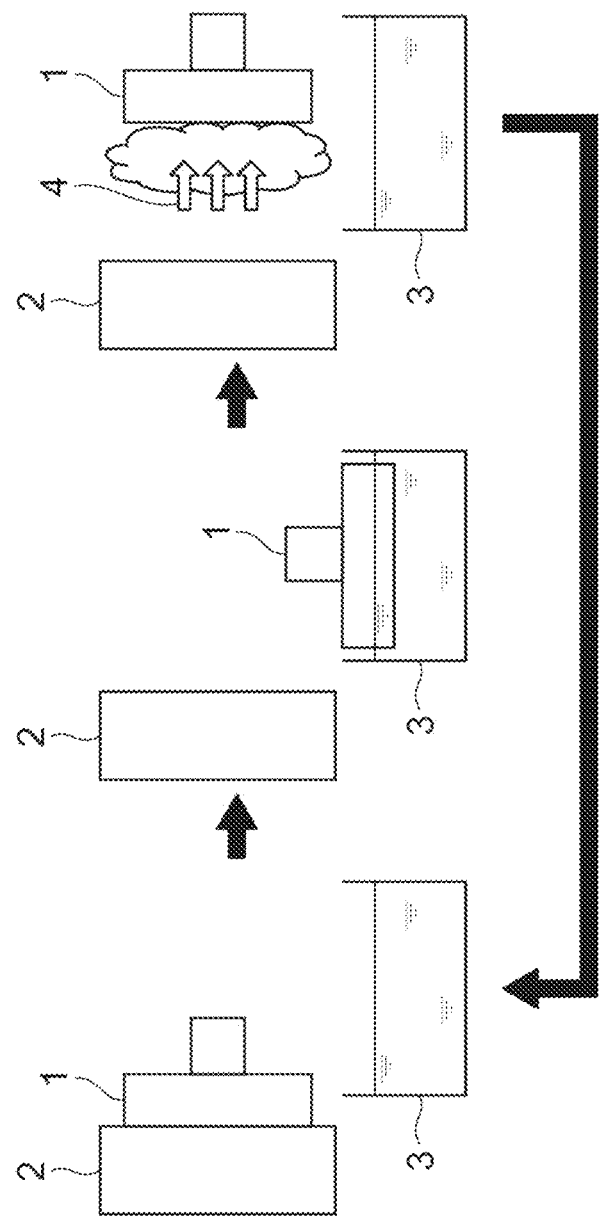
FIG. 2 is a diagram for explaining a thermal fatigue test.

The residual stress imparted to the object by the shot peening is reduced by thermal fatigue. For example, in a die casting mold, the thermal fatigue occurs due to repeated thermal expansion caused by heating with a molten metal and heat shrinkage caused by cooling with a mold release agent. FIG. 2 is a diagram for explaining a thermal fatigue test. In this thermal fatigue test, the thermal fatigue of the die casting mold is reproduced. As shown in FIG. 2, in this thermal fatigue test, first, a test piece 1 is pressed against a surface of a heater 2. The time for pressing the test piece 1 is set to 150 seconds. The temperature of the heater 2 is set such that the surface temperature of the test piece 1 is 570° C. Then, the test piece 1 is cooled with water 3 at room temperature. Subsequently, the test piece 1 is dried by an air blower that blows air 4. The above one cycle takes 3 minutes and is repeated.

The material of the test piece 1 is SKD61 (JIS standard), which is a hot tool steel. SKD61 of the JIS standard corresponds to X40CrMoV5-1 of the ISO standard (ISO 4957: 1999). The chemical composition (wt %) of the test piece 1 is shown in Table 1. The test piece 1 was prepared by quenching and tempering, and then performing soft nitriding in a salt bath. The shape of the test piece 1 is a disc shape having a thickness of 15 mm and a diameter of 58 mm ($\varphi$58), and, as a grip portion thereof, a cylinder having a height of 15 mm and a diameter of 15 mm ($\varphi$15) was provided.

TABLE 1

|       | C   | Si  | Mn  | Cr  | Mo  | V   |
|-------|-----|-----|-----|-----|-----|-----|
| SKD61 | 0.4 | 1.0 | 0.4 | 5.2 | 1.2 | 0.8 |

Figure 3:
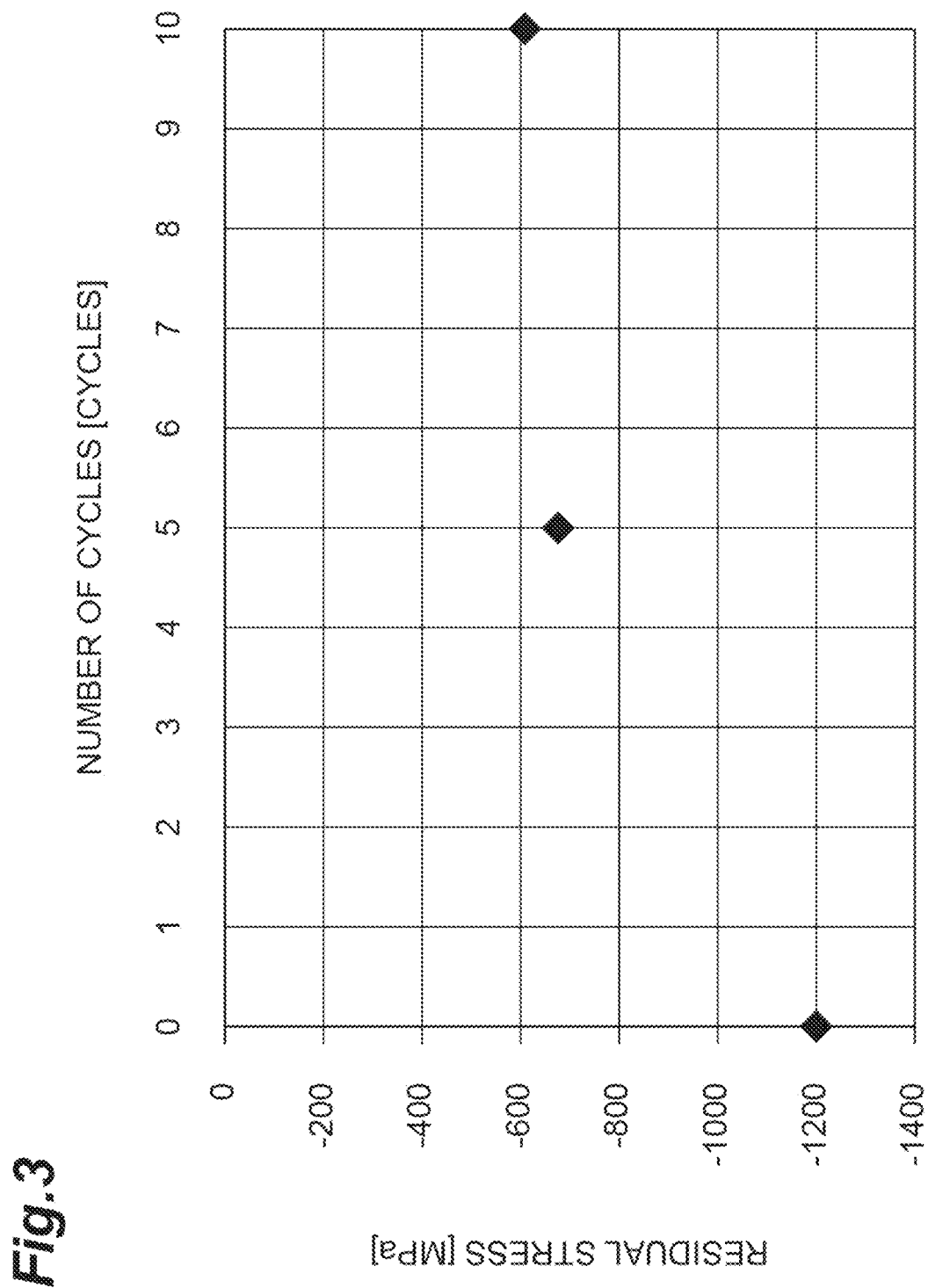
FIG. 3 is a graph showing a change in residual stress as a result of a first cycle test.

FIG. 3 is a graph showing a change in residual stress as a result of a first cycle test. The horizontal axis of the graph is the number of cycles of the above-mentioned thermal fatigue test, and the vertical axis thereof is the residual stress (MPa) of the test piece 1 (see FIG. 2). The first cycle test is a thermal fatigue test of an extremely low cycle up to 10 cycles, and was performed after the shot peening was performed on the test piece 1 under the condition for imparting the maximum residual stress. The residual stress and half-value range were measured at each time before the start of the first cycle test, after the end of 5 cycles, and at the end of 10 cycles. The residual stress and half-value range were measured by the X-ray diffraction method under the measurement conditions shown in Table 2. As shown in FIG. 3, as the number of cycles increased, the residual stress decreased due to thermal fatigue. The half-value range will be described later.

TABLE 2

| Method | cos α method |
|---|---|
| Characteristic X ray | Crk α |
| Collimator | $\varphi$ 1.0 |
| X ray incidence angle | 35 deg |
| Diffraction angle 2θ | 156.396 deg |
| Diffraction plane (hkl) | (211) |
| X ray stress measurement constant | −465.097 GPa |

Based on this, the measurement of the first residual stress is performed before applying thermal fatigue, which is a factor for reducing the first residual stress, to the object after the first shot peening. Accordingly, the measurement accuracy of the first residual stress imparted by the first shot peening can be improved.

In step S4, the second shot peening is performed on the object after step S3 under the shot peening condition determined in step S1. Accordingly, the residual stress is imparted to the surface portion of the object.

In step S5, the second residual stress of the object after step S4 is measured. As mentioned above, the residual stress is reduced by thermal fatigue. Therefore, similar to the measurement of the first residual stress, the measurement of the second residual stress is performed before applying thermal fatigue, which is a factor for reducing the second residual stress, to the object after the second shot peening. Accordingly, the measurement accuracy of the second residual stress imparted by the second shot peening can be improved. Similar to step S3, in step S5, the second residual stress is measured by the diffraction method, for example. In step S5, the measurement may be performed by the positron annihilation method.

In step S6, the deterioration of the metal material forming the object is evaluated based on the first residual stress measured in step S3 and the second residual stress measured in step S5. That is, in step S6, the deterioration of the metal material forming the object is evaluated based on the magnitude of the difference between the second residual stress and the first residual stress.

Figure 4:
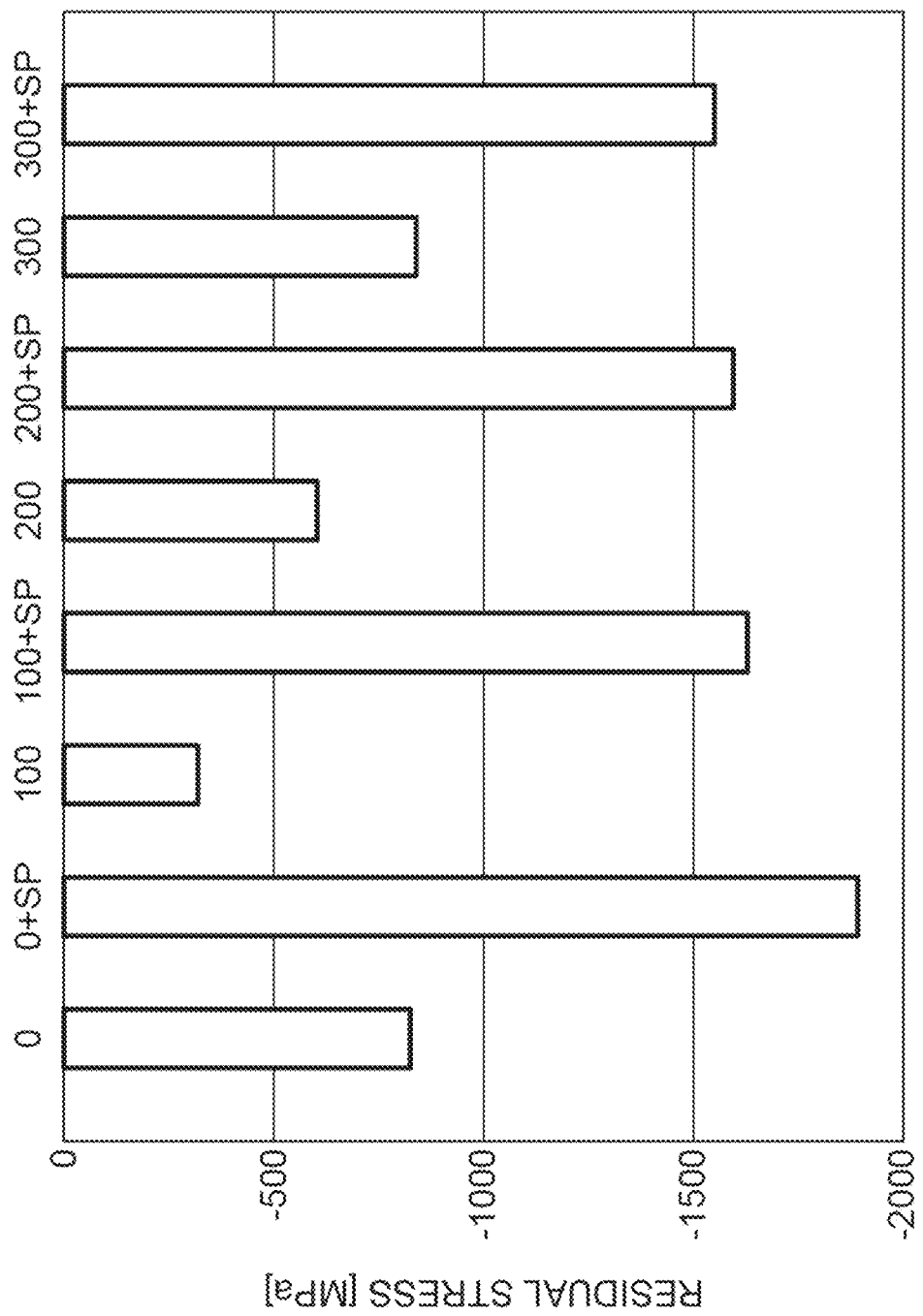
FIG. 4 is a graph showing a change in residual stress as a result of a second cycle test.

FIG. 4 is a graph showing a change in residual stress as a result of the second cycle test. In the second cycle test, a thermal fatigue test of the low cycle was performed in units of 100 cycles up to 300 cycles after the shot peening was performed on the test piece 1 under the condition for imparting the maximum residual stress. The shot peening was performed again every 100 cycles of the thermal fatigue test, and the residual stress and the half-value range were measured before and after the shot peening. The numbers on the horizontal axis of the graph of FIG. 4 indicate the number of cycles of the thermal fatigue test, and "SP" indicates after shot peening. The vertical axis is the residual stress (MPa) of the test piece 1. The half-value range will be described later.

As shown in FIG. 4, when a case after the shot peening and before the thermal fatigue test (the horizontal axis "0+SP") and a case after 100 cycles (the horizontal axis "100") are compared with each other, it is understood that the residual stress is attenuated by about 1500 MPa. The residual stress is imparted up to about −1600 MPa by performing re-shot peening (the horizontal axis "100+SP"), but the residual stress that can be imparted decreases. After that, the thermal fatigue test and the re-shot peening are repeated every 100 cycles up to 300 cycles, but the value of the residual stress that can be imparted gradually decreases.

Non-Patent Literature 1 shows that the maximum residual stress after the shot peening is about 60% of the 0.2% proof stress. Non-Patent Document 2 shows that the residual stress after the shot peening is about half of the proof stress (the yield stress). As shown in FIG. 4, the fact that the residual stress after performing the re-shot peening is reduced means that the metal material itself forming the test piece 1 deteriorates due to the thermal fatigue and the proof stress is reduced. Therefore, the deterioration of the metal material forming the object can be evaluated in a non-destructive manner based on the magnitude of the difference between the second residual stress and the first residual stress.

As described above, in the deterioration evaluation method according to the embodiment, the phenomenon that when the object formed of the metal material deteriorates, even if the shot peening is performed under the shot peening condition for imparting the maximum residual stress, the value of the residual stress which is measured after the shot peening decreases is used. Accordingly, it is possible to easily evaluate the deterioration of the metal material forming the object in a non-destructive manner based on the first residual stress measured after the first shot peening (that is, after step S2) and the second residual stress measured after the second shot peening (that is, after step S4).

Specifically, a threshold value for the ratio between the first residual stress and the second residual stress can be set in advance, and the threshold value can be used to evaluate the deterioration of the object. Accordingly, it is possible to determine, for example, the replacement time of the object. That is, it is possible to determine the replacement time of the object by predicting the time when the ratio between the first residual stress and the second residual stress becomes equal to or less than the threshold value set in advance. This prediction can be performed based on, for example, the relationship between the ratio between the residual stress measured at the time of manufacturing the object and the residual stress measured at the time of regular maintenance of the object, and the usage count (or the usage period) of the object from the time of manufacturing to the time of regular maintenance. Instead of the ratio between the first residual stress and the second residual stress, a threshold value for the difference between the first residual stress and the second residual stress, or the like may be set in advance, and the threshold value may be used to evaluate the deterioration of the object.

In step S1, the shot peening condition is determined based on the hardness of the object, so that the shot peening condition can be appropriately determined. In steps S3 and S5, the measurement is performed by the diffraction method, so that the measurement can be appropriately performed. Since steel materials, of which the object is one, are widely used, there is a high need for the deterioration evaluation method.

In the deterioration evaluation method according to the embodiment, the shot peening step is performed a plurality of times (at least twice), so that the residual stress is imparted to the object a plurality of times (at least twice). Accordingly, the life of the object can be extended.

The present invention is not necessarily limited to the above-described embodiment, and various modifications can be made without departing from the gist thereof.

In the deterioration evaluation method according to the embodiment, instead of the residual stress, the half-value range may be measured. That is, in step S1, instead of the maximum residual stress, the shot peening condition for imparting the maximum half-value range is determined. Since the maximum residual stress is the maximum half-value range, the shot peening condition for imparting the maximum residual stress is the same as the shot peening condition for imparting the maximum half-value range. Therefore, step S1 is substantially the same in both cases. In step S3, instead of measuring the first residual stress of the object after the first shot peening (that is, after step S2), a first half-value range of the object after the first shot peening is measured. In step S5, instead of measuring the second residual stress of the object after the second shot peening (that is, after step S4), a second half-value range of the object after the second shot peening is measured. In step S6, instead of evaluating the deterioration of the object based on the first residual stress and the second residual stress, the deterioration of the object is evaluated based on the first half-value range and the second half-value range.

Figure 5:
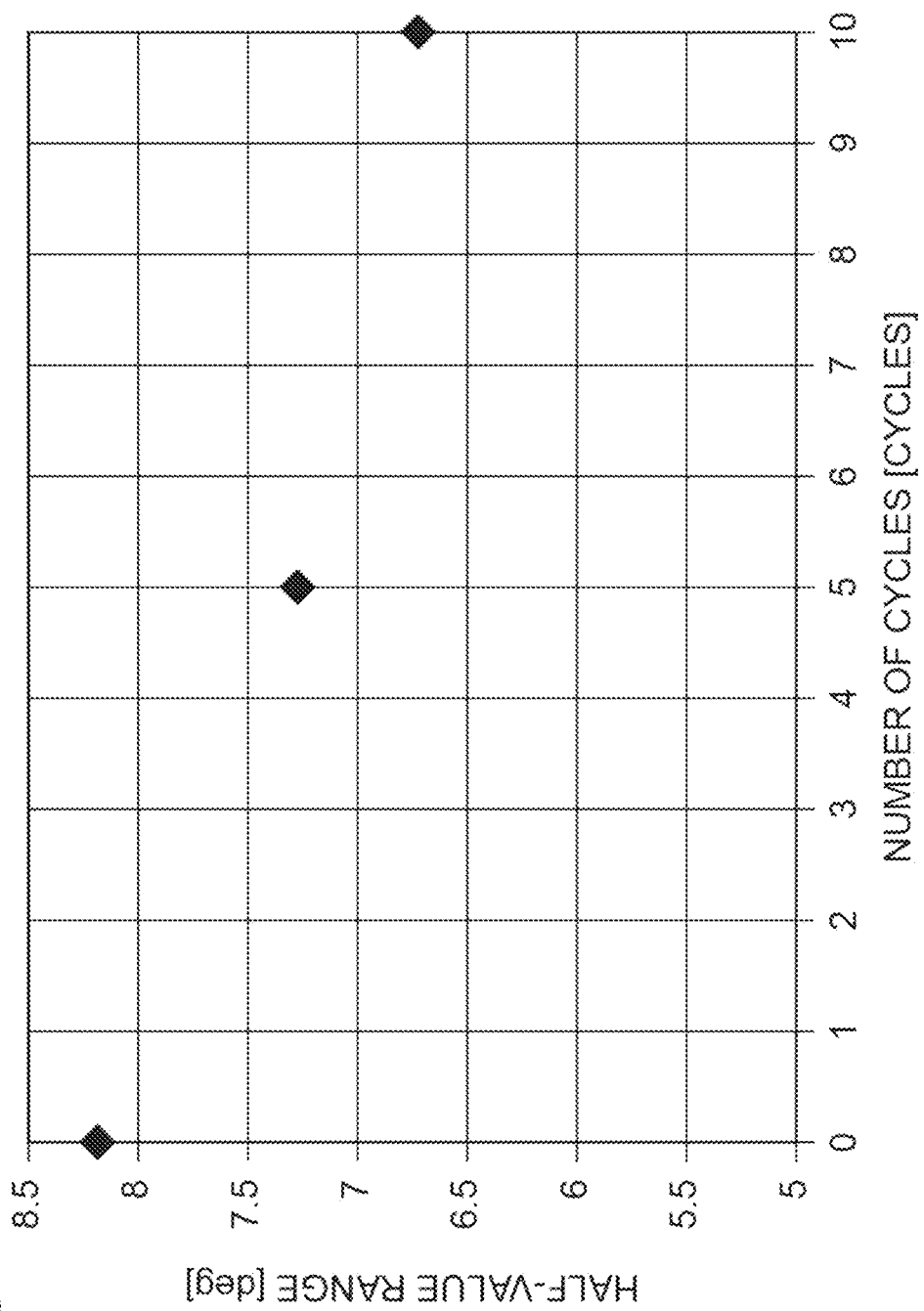
FIG. 5 is a graph showing a change in half-value range as a result of the first cycle test.

FIG. 5 is a graph showing a change in half-value range as a result of the first cycle test. The first cycle test is as described above. The horizontal axis of the graph is the same as in FIG. 3, and the vertical axis is the half-value range (deg) of the test piece 1 (see FIG. 2). As shown in FIG. 5, as the number of cycles increased, the half-value range decreased due to thermal fatigue. Based on this, the measurement of the first half-value range is performed before applying thermal fatigue, which is a factor for reducing the first half-value range, to the object after the first shot peening. Accordingly, the measurement accuracy of the first half-value range imparted by the first shot peening can be improved. Similarly, the measurement of the second half-value range is performed before applying thermal fatigue, which is a factor for reducing the second half-value range, to the object after the second shot peening. Accordingly, the measurement accuracy of the second half-value range imparted by the second shot peening can be improved.

Figure 6:
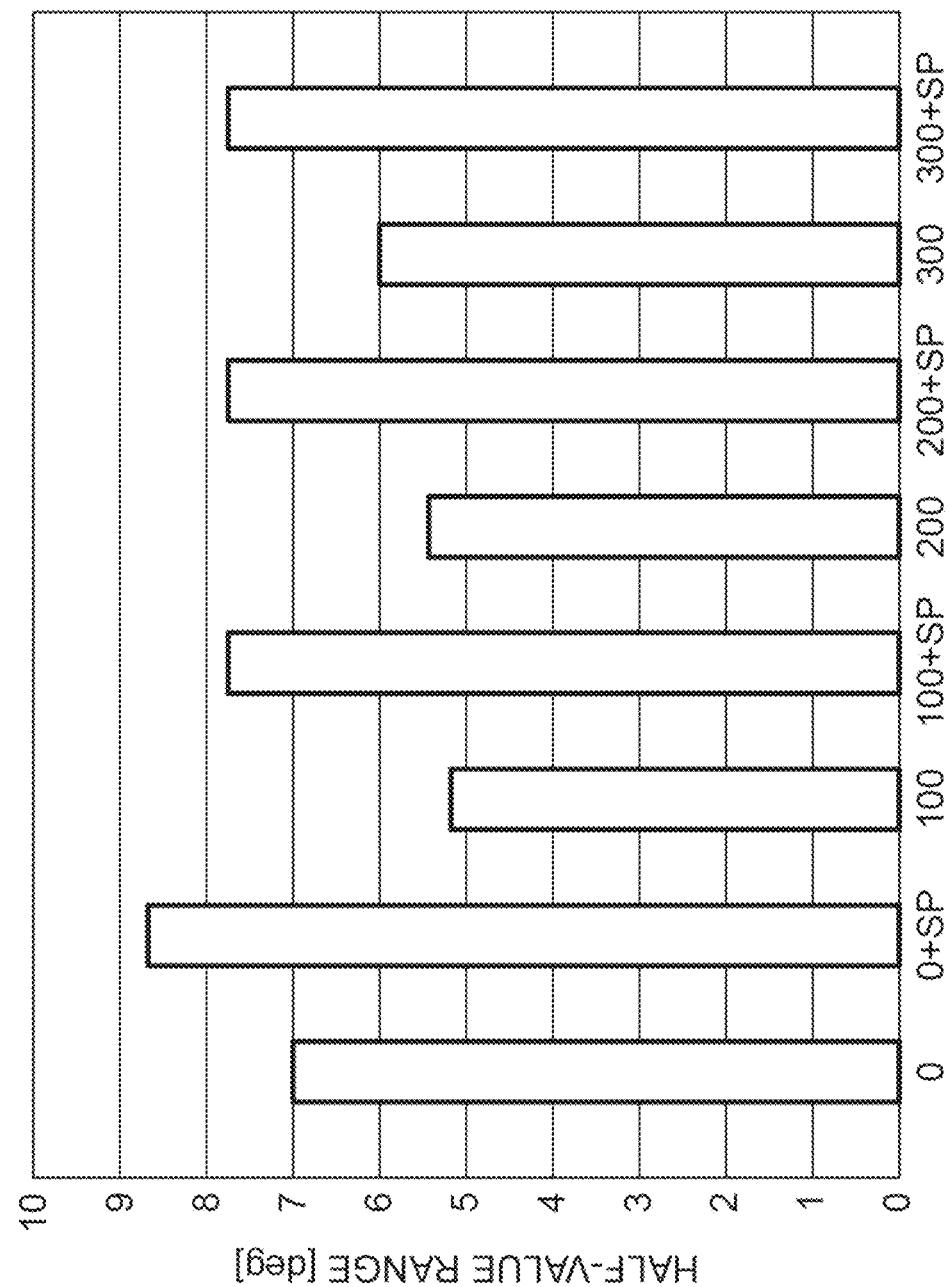
FIG. 6 is a graph showing a change in half-value range as a result of the second cycle test.

FIG. 6 is a graph showing a change in half-value range as a result of the second cycle test. The second cycle test is as described above. The horizontal axis of the graph is the same as in FIG. 3, and the vertical axis is the half-value range (deg) of the test piece 1 (see FIG. 2). As shown in FIG. 6, as compared with a case after the shot peening and before the thermal fatigue test (the horizontal axis "0+SP"), in a case after 100 cycles (horizontal axis "100"), the half-value range is significantly reduced. The half-value range is recovered up to the 7-degree range by the re-shot peening (the horizontal axis "100+SP"). Although the half-value range is recovered by the re-shot peening, it does not reach the value of the half-value range introduced at the initial stage (the horizontal axis "0+SP").

In a case of measuring the half-value range instead of the residual stress in this way, when the object formed of the metal material deteriorates, even if the shot peening is performed under the shot peening condition for imparting the maximum half-value range, the value of the half-value range which is measured after the shot peening decreases. Accordingly, it is possible to evaluate the deterioration of the object in a non-destructive manner based on the first half-value range measured after the first shot peening (that is, after step S2) and the second half-value range measured after the second shot peening (that is, after step S4).

In the deterioration evaluation method according to the embodiment, the shot peening is performed twice and the deterioration of the object is evaluated based on two residual stresses or half-value ranges, but the shot peening may be performed three times or more, and the deterioration of the object may be evaluated based on three or more residual stresses or half-value ranges. That is, the deterioration evaluation method according to the embodiment may further include a third shot peening step, a third measurement step, and the like. Accordingly, the deterioration of the object can be evaluated more accurately.

REFERENCE SIGNS LIST

1 Test piece
2 Heater
3 Water
4 Air

The invention claimed is:

1. A deterioration evaluation method comprising:
   a determination step of determining a shot peening condition for imparting a maximum residual stress to an object formed of a metal material;
   a first shot peening step of performing first shot peening on the object under the shot peening condition;
   a first measurement step of measuring a first residual stress of the object after the first shot peening step;

a second shot peening step of performing second shot peening on the object after the first measurement step under the shot peening condition;

a second measurement step of measuring a second residual stress of the object after the second shot peening step; and an evaluation step of evaluating deterioration of the object based on the first residual stress and the second residual stress.

2. The deterioration evaluation method according to claim 1, wherein, in the determination step, the shot peening condition is determined based on a hardness of the object.

3. The deterioration evaluation method according to claim 2, wherein, in the first measurement step and the second measurement step, a measurement is performed by a diffraction method.

4. The deterioration evaluation method according to claim 2, wherein the object is formed of a steel material.

5. The deterioration evaluation method according to claim 1, wherein, in the first measurement step and the second measurement step, a measurement is performed by a diffraction method.

6. The deterioration evaluation method according to claim 5, wherein the object is formed of a steel material.

7. The deterioration evaluation method according to claim 1, wherein the object is formed of a steel material.

8. A deterioration evaluation method comprising:
a determination step of determining a shot peening condition for imparting a maximum half-value range to an object formed of a metal material;

a first shot peening step of performing first shot peening on the object under the shot peening condition;

a first measurement step of measuring a first half-value range of the object after the first shot peening step;

a second shot peening step of performing second shot peening on the object after the first measurement step under the shot peening condition;

a second measurement step of measuring a second half-value range of the object after the second shot peening step; and an evaluation step of evaluating deterioration of the object based on the first half-value range and the second half-value range.

9. The deterioration evaluation method according to claim 8, wherein, in the determination step, the shot peening condition is determined based on a hardness of the object.

10. The deterioration evaluation method according to claim 8, wherein, in the first measurement step and the second measurement step, a measurement is performed by a diffraction method.

11. The deterioration evaluation method according to claim 8, wherein the object is formed of a steel material.

* * * * *